United States Patent
Zuo et al.

(10) Patent No.: US 11,766,440 B1
(45) Date of Patent: Sep. 26, 2023

(54) METHODS FOR THE PREVENTION AND TREATMENT OF HEARING LOSS

(71) Applicant: Ting Therapeutics LLC, Omaha, NE (US)

(72) Inventors: Jian Zuo, Omaha, NE (US); Zhuo Li, Omaha, NE (US)

(73) Assignee: Ting Therapeutics LLC, Omaha, NE (US)

( * ) Notice: Subject to any disclaimer, the term of this patent is extended or adjusted under 35 U.S.C. 154(b) by 0 days.

(21) Appl. No.: 18/117,852

(22) Filed: Mar. 6, 2023

Related U.S. Application Data

(60) Division of application No. 18/084,033, filed on Dec. 19, 2022, which is a continuation of application No. PCT/US2021/041197, filed on Jul. 10, 2021.

(60) Provisional application No. 63/050,568, filed on Jul. 10, 2020.

(51) Int. Cl.
| | |
|---|---|
| *A61K 31/5377* | (2006.01) |
| *A61P 27/16* | (2006.01) |
| *A61K 33/243* | (2019.01) |
| *A61K 31/7036* | (2006.01) |

(52) U.S. Cl.
CPC ...... *A61K 31/5377* (2013.01); *A61K 31/7036* (2013.01); *A61K 33/243* (2019.01); *A61P 27/16* (2018.01)

(58) Field of Classification Search
CPC .......................... A61K 31/5377; A61P 27/16
See application file for complete search history.

(56) References Cited

U.S. PATENT DOCUMENTS

| | | | |
|---|---|---|---|
| 8,420,595 | B2 | 4/2013 | Kopke et al. |
| 9,572,815 | B2 | 2/2017 | Zuo et al. |
| 2004/0110719 | A1 | 6/2004 | Campbell |
| 2008/0280955 | A1 | 11/2008 | McCamish |
| 2013/0085112 | A1 | 4/2013 | Collard et al. |
| 2014/0235631 | A1 | 8/2014 | Bunt et al. |
| 2016/0089371 | A1 | 3/2016 | Liu et al. |
| 2017/0327557 | A1 | 11/2017 | Chen |
| 2018/0161340 | A1 | 6/2018 | Zuo et al. |
| 2020/0093923 | A1 | 3/2020 | Zuo et al. |

FOREIGN PATENT DOCUMENTS

| | | | |
|---|---|---|---|
| WO | WO 2016092375 | * | 6/2016 |
| WO | 2016114655 A1 | | 7/2016 |
| WO | 2018204764 A1 | | 11/2018 |

OTHER PUBLICATIONS

Atkinson et al. "hair Cell Regeneration after ATOH1 Gene Therapy in the Cochlea of Profoundly Deaf Adult Guinea Pigs," PLoS One, Jul. 18, 2014 (Jul. 18, 2014), vol. 9, Iss. 7, pp. 1-11. entire document.
Boanza et al. "A primary role fo the epidermal growth factor receptor in ommatidial spacing in the *Drosophila* eye," Current Biology, Mar. 20, 2001 (Mar. 20, 2001), vol. 9, Iss. 6, pp. 396-404. entire document.
Dabestani et al, Drug Repurposing of an EGF Inhibitor for Protection Against Noise-Induced Hearing Loss. 2020. Creighton University, M.Sc. Thesis. ProQuest, PQ No. 28001904; http://hld.handle.net/10504/127028.
Fereydoun Sajjadi, International Preliminary Report on Patentability, PCT, dated Feb. 8, 2023, 18, PCT.
Jarman et al. "The role of Atonal transcription factors in the development of mechanosensitive cells," Seminars in Cell and Developmental Biology, May 1, 2013 (May 1, 2013), vol. 24, Iss. 5, pp. 438-447. entire document.
Kim, Harry. International Search Report of the ISA. PCT, dated Apr. 28, 2022. 1-3.
Kim, Harry. Written Opinion of the ISA. PCT, dated Apr. 28, 2022. 1-6.
Ng et al. Phase 1 dose-escalation study of momelotinib, a Janus Kinase 1/2 inhibitor, combined with gemcitabine and nab-paclitaxel in patients with previously untreated metastatic pancreatic ductal adenocarcinoma. Investigational New Drugs, Jul. 30, 2018,, vol. 37, pp. 159-165, [retrieved on Apr. 6, 2022], Retrieved from the Internet. entire document.
Teitz et al., "CDK2 inhibitors as candidate therapeutics for cisplatin- and noise-induced hearing loss," J. Exp. Med. Apr. 2, 2018, vol. 215, No. 4, pp. 1187-1203.
PCT/IPEA/416 for US2021/041197 dated Apr. 28, 2022.

* cited by examiner

*Primary Examiner* — Noble E Jarrell
(74) *Attorney, Agent, or Firm* — Veritay Group IP; Susan Fentress

(57) ABSTRACT

In one aspect, use of compounds as active agents to treat a hearing impairment and to prevent a hearing impairment, and methods of treating and/or preventing hearing impairments or disorders using the compositions are disclosed. Momelotinib and Fedratinib exhibit excellent protection against antibiotic-induced hearing loss in zebrafish and mice when administered prophylactically. In one aspect, Momelotinib or Fedratinib can be used as a therapy for the treatment and/or prevention of hearing loss. This abstract is intended as a scanning tool for purposes of searching in the particular art and is not intended to be limiting of the present invention.

8 Claims, 5 Drawing Sheets

METHODS FOR THE PREVENTION AND TREATMENT OF HEARING LOSS

Cross-reference to related applications: This application is a divisional patent application of U.S. Ser. No. 18/084,033, which is a continuation of PCT/US21/41197 filed Jul. 10, 2021 and claims the benefit of U.S. provisional patent application Ser. No. 63/050,568 filed Jul. 10, 2020, under 35 USC § 119(e) and 35 U.S.C. § 111(a) (hereby specifically incorporated herein by reference).

Statement regarding federally sponsored research or development: This invention was made with government support under NIH/NIDCD 1R43DC019065, NIH/NIDCD R01DC015444, Office of Naval Research (ONR) N00014-18-1-2507, Department of Defense (DoD)/USAMRMC-RH170030. The government has certain rights in the invention

BACKGROUND OF THE INVENTION

(1) Field of the Invention

The present invention relates to therapeutic uses of compounds for treating, inhibiting, and/or preventing loss of hearing.

(2) Description of Related Art Including Information Disclosed Under 37 CFR 1.97 and 37 CFR 1.98

Over 35 million Americans suffer from hearing impairment. In mammals, hair cell impairment is permanent. Antibiotic-induced hearing impairment (NIHL) is a permanent side effect from often necessary medical care. Neonates admitted to the neonatal intensive care unit have ten times the rate of hearing loss as neonates not admitted, often associated with the administration of antibiotics. The spiral-shaped cochlea of the inner ear is responsible for detecting sound. Inner hair cells lining the cochlea transform the mechanical vibrations of sound waves into chemical signals. These chemicals are then released from the hair cells and received by receptors on the auditory nerve fibers that send electrical impulses to the brain. The inner ear cells lining the cochlea can be destroyed by the use of antibiotics, leading to a condition called sensorineural hearing impairment.

Currently, there are no clinically proven medications for the treatment of hearing impairment (sensorineural and neural), or tinnitus associated with the inner ear, and a medication that could be used to prevent, alleviate, or eliminate hearing impairment (or tinnitus) would thus be very desirable. The most common remedy for individuals suffering from severe sensorineural hearing impairment is a hearing aid, which functions to amplify sound. Hearing aids are non-invasive and can improve an individual's ability to hear. However, hearing aids can often be quite conspicuous and embarrassing to the wearer and hearing aids do not return hearing to normal levels.

Furthermore, hearing aids amplify sound indiscriminately, sometimes amplifying sounds that an individual does not wish to hear, such as environmental noise.

There exists a need in the art for a solution to hearing impairment due to antibiotics.

BRIEF SUMMARY OF THE INVENTION

The invention provides a method to prevent or treat hearing loss including the steps of administering to an animal in need thereof an effective amount of a pharmaceutical composition containing a therapeutically active agent, wherein the therapeutically active agent includes: momelotinib, fedratinib, axitinib, sunitinib, ruxolitinib, AZD1480, AT9283, WP1066, WHI-P154, ZM 39923 HCL, oclacitinib maleate, deucravacitinib, itacitinib, solcitinib, ritlecitinib, WHI-P97, SAR-20347, filgotinib, decernotibnib, glpg0634, PF-06826647, and JANEX-1.

The inventive subject matter also includes a composition for use in preventing or treating hearing loss by protecting inner ear cells from death wherein the composition is an effective amount of an active agent, wherein the active agent includes: momelotinib, fedratinib, axitinib, sunitinib, ruxolitinib, AZD1480, AT9283, WP1066, WHI-P154, ZM 39923 HCL, oclacitinib maleate, deucravacitinib, itacitinib, solcitinib, ritlecitinib, WHI-P97, SAR-20347, filgotinib, decernotibnib, glpg0634, PF-06826647, and JANEX-1 or a pharmaceutically acceptable salt thereof.

The inventive subject matter also includes a kit made of an active agent, wherein the active agent includes: momelotinib, fedratinib, axitinib, sunitinib, ruxolitinib, AZD1480, AT9283, WP1066, WHI-P154, ZM 39923 HCL, oclacitinib maleate, deucravacitinib, itacitinib, solcitinib, ritlecitinib, WHI-P97, SAR-20347, filgotinib, decernotibnib, glpg0634, PF-06826647, and JANEX-1 or a pharmaceutically acceptable salt thereof; and one or more of:.(A) at least one antibiotic;(B) at least one cancer drug (C)instructions for preventing a hearing impairment.

BRIEF DESCRIPTION OF THE SEVERAL VIEWS OF THE DRAWING

The accompanying figures, which are incorporated in and constitute a part of this specification, illustrate several aspects and together with the description serve to explain the principles of the invention.

DETAILED DESCRIPTION OF THE INVENTION

Figure 1:
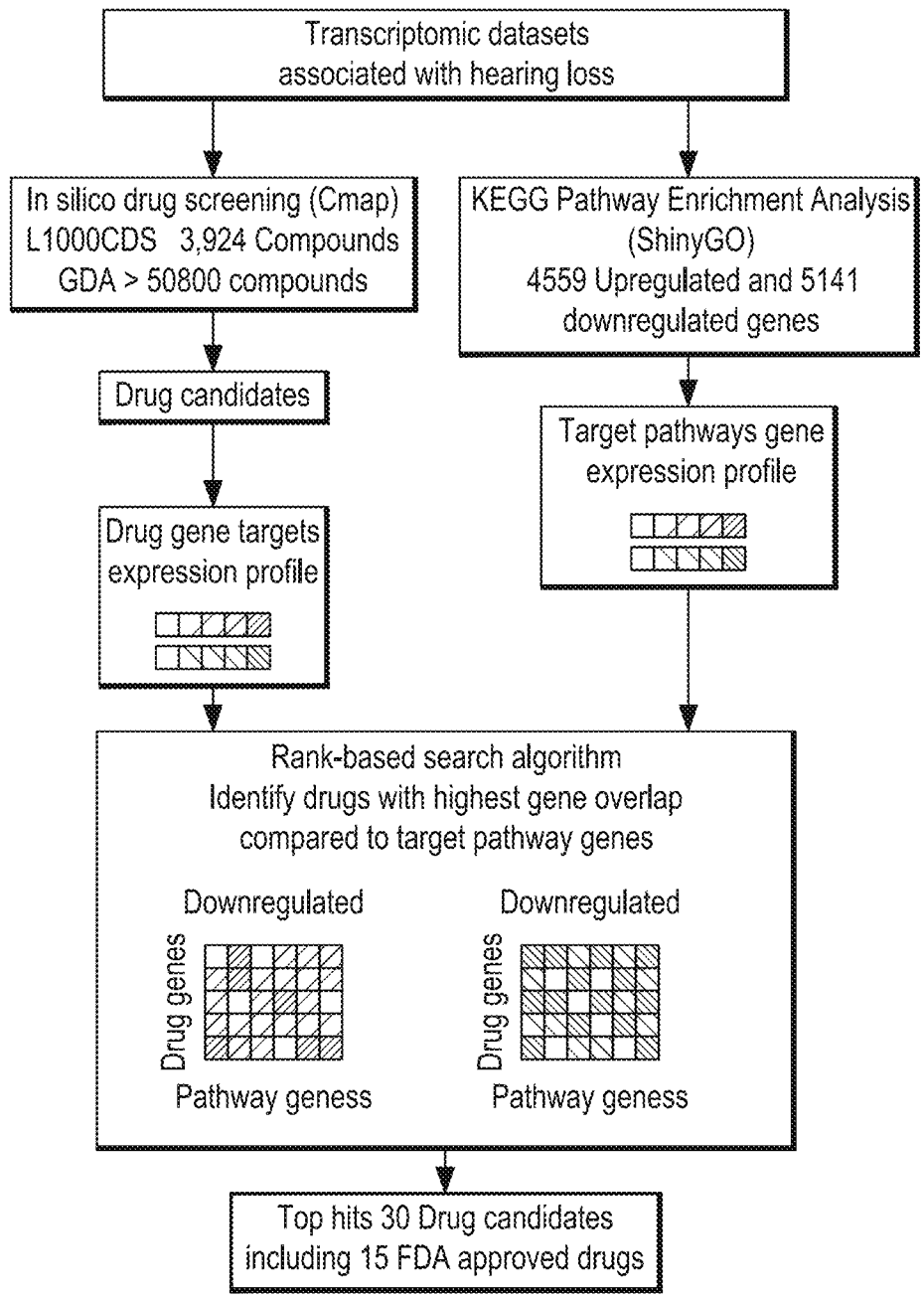
FIG. 1 is a schematic diagram showing how compounds of this invention were identified based on a comparison of data sets from drug screen connectivity maps and pathway enrichment analysis revealing drugs acting against hearing loss.

The present invention can be understood more readily by reference to the following detailed description of the invention and the Examples included therein. Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

Now referring to FIG. 1 compounds were identified based on a comparison of data sets from drug screen connectivity maps and pathway enrichment analysis revealing compounds acting against hearing loss. This method was developed to derive drug candidates from a diverse chemical space, covering a wide range of biological pathways, avoiding bias associated with focusing on previously reported pathways. The resulting compounds exhibited overlaps in gene expression transcriptomic profiles between at least one of a plurality of cell-lines or mouse strains treated with ototoxic insults (cisplatin, noise, or antibiotic exposure and at least one of a plurality of cell-lines or mouse strains treated with one of the compounds.

Here specifically, the data set sought was conformity to a NIHL-resistant mouse strains to NIHL sensitive mouse strains (129SvJ and CAST). Here specifically the data set sought was conformity to cisplatin-resistant and sensitive cancer cell lines, HEI-OC1 cell line, in vivo mouse cochlear single cell RNA seq with and without cisplatin treatment. However, the data set greatest weigh was transcriptome perturbation of neonatal mouse organ of *Corti* exposed to gentamicin for damage related to antibiotic treatment. These compounds with an overlap of the data sets include as the therapeutically active agent: momelotinib, fedratinib, axitinib, sunitinib, ruxolitinib, AZD1480, AT9283, WP1066, WHI-P154, ZM 39923 HCL, oclacitinib maleate, deucravacitinib, itacitinib, solcitinib, ritlecitinib, WHI-P97, SAR-20347, filgotinib, decernotibnib, glpg0634, PF-06826647, and JANEX-1.

Compounds are revealed to protect against hair cell apoptosis. Compounds are identified as acting against hair cell loss in animals by the models and data presented. Models reveal properties necessary for an otoprotective compound such as high efficacy against hair cell loss, relatively low toxicity. Compounds are revealed to have high efficacy and high affinity in mouse and zebrafish models used to demonstrate protection against hair cell loss. The lateral-line neuromasts of zebrafish are a valuable model for testing compounds protective against hearing loss in vivo, as their HCs are considered homologous to those in the mammalian inner ear and are readily accessible to drugs in vivo. Teitz et al., J. Exp. Med. 2;215(4):1187-1203 (2018). Mouse models involving HEI-OC1 have shown effective in validating therapeutic uses of compounds against hearing loss due to cancer treatment such as cisplatin, noise, antibiotics, and aging. Teitz et al., J. Exp. Med. 2;215(4):1187-1203 (2018).

The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration. Compounds can be synthesized by a variety of methods known in the art.

Fedratinib is an FDA-approved therapy for patients with myeloproliferative neoplasm-associated myelofibrosis. Momelotinib is in phase 3 clinical trials for the treatment of patients with intermediate- or high-risk myelofibrosis who previously received a JAK inhibitor.

AZD1480 a novel ATP-competitive JAK2 inhibitor with IC50 of 0.26 nM in a cell-free assay, selectivity against JAK3 and Tyk2, and to a smaller extent against JAK1. AT9283 is a potent JAK2/3 inhibitor with IC50 of 1.2 nM/1.1 nM in cell-free assays; also potent to Aurora NB, Abl1(T315I). WP1066 is a novel inhibitor of JAK2 and STAT3 with IC50 of 2.30 μM and 2.43 μM in HEL cells; shows activity to JAK2, STAT3, STAT5, and ERK1/2 not JAK1 and JAK3. WP1066 induces apoptosis. WHI-P154 is a potent JAK3 inhibitor with IC50 of 1.8 μM, no activity against JAK1 or JAK2, also inhibits EGFR, Src, Abl, VEGFR and MAPK, prevents Stat3, but not Stat5 phosphorylation. ZM 39923 HCl is an JAK1/3 inhibitor with pIC50 of 4.4/7.1, almost no activity to JAK2 and modestly potent to EGFR; and is sensitive to transglutaminase.

Oclacitinib maleate (PF-03394197) is a novel inhibitor of JAK family members with IC50 ranging from 10 to 99 nM and JAK1-dependent cytokines with IC50 ranging from 36 to 249 nM. It does not inhibit a panel of 38 non-JAK kinases. Deucravacitinib (BMS-986165) is a highly potent and selective allosteric inhibitor of Tyk2 with a Ki value of 0.02 nM for binding to the Tyk2 pseudokinase domain. It is highly selective against a panel of 265 kinases and pseudokinases. Itacitinib (INCB39110) is an orally bioavailable inhibitor of Janus-associated kinase 1 (JAK1) with potential antineoplastic activity. Solcitinib (GLPG0778, GSK2586184) is an inhibitor of JAK1 with an IC50 of 8-9 nM, and shows 11-, 55- and 23-fold selectivity over JAK2, JAK3 and TYK2, respectively. Ritlecitinib (PF-06651600) is a potent and irreversible JAK3-selective inhibitor with an IC50 of 33.1 nM but without activity (IC50>10,000 nM) against JAK1, JAK2, and TYK2.

WHI-P97 is a potent inhibitor of JAK-3 with an estimated Ki value of 0.09 μM in modeling studies and a measured IC50 value of 2.5 μM in EGFR kinase inhibition assays. SAR-20347 is a potent inhibitor of TYK2, JAK1, JAK2 and JAK3 with IC50 of 0.6 nM, 23 nM, 26 nM, and 41 nM, respectively. SAR-20347 inhibits TYK2- and JAK1-mediated IL-12 and IFN-α signaling. Filgotinib (GLPG0634) is a selective JAK1 inhibitor with IC50 of 10 nM, 28 nM, 810 nM, and 116 nM for JAK1, JAK2, JAK3, and TYK2, respectively. Decernotinib (VX-509) is a potent and selective JAK3 inhibitor with Ki of 2.5 nM, >4-fold selectivity over JAK1, JAK2, and TYK2, respectively.

GLPG0634 analogue is a selective JAK1 inhibitor with IC50 of 10 nM, 28 nM, 810 nM, and 116 nM for JAK1, JAK2, JAK3, and TYK2, respectively. PF-06826647 (Tyk2-IN-8, compound 10) is a selective and orally administered inhibitor of tyrosine kinase 2 (TYK2) with IC50 of 17 nM for binding to TYK2 catalytically active JH1 domain. PF-06826647 (Tyk2-IN-8, compound 10) also inhibits JAK1 and JAK2 with IC50 of 383 nM and 74 nM, respectively. PF-06826647 (Tyk2-IN-8, compound 10) is used in the treatment of psoriasis (PSO). JANEX-1 (WHI-P131) is a small molecule inhibitor of JAK3 that selectively inhibits JAK3 at an IC50 of 78 μM without altering the activity of JAK1 or JAK2, or any other protein tyrosine kinases (IC50 350 μM).

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions include the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas.

The pharmaceutical compositions of the present invention include the compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Figure 2A:
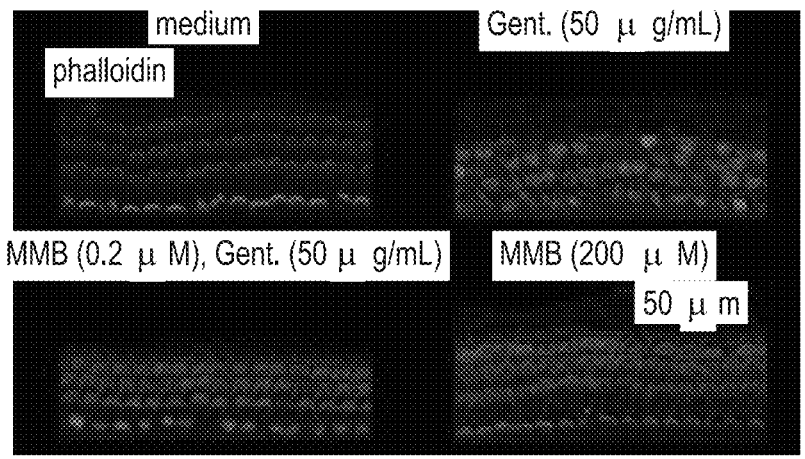
FIGS. 2A-B shows outer hair cell protection by Momelotinib against aminoglycosides. A) Representative confocal images of the middle turn of whole-mount cochlear explants from P3 FVB mice treated with medium alone, 50 mg/mL gentamicin, 0.2 µM Momelotinib and 50 mg/mL gentamicin for 24 h. 0.2 µM Momelotinib alone did not show toxicity to HCs. HCs are labeled with phalloidin. B) shows outer hair cell (OHC) survival (OHC number per 100 µm length of cochlear middle turn) after treatment with various concentration of Momelotinib and 50 mg/mL gentamicin or 600 mM kanamycin. (Mann-Whitney U Test, *P<0.05, **P<0.01) shown in a micromolar concentration.
Figure 2B:
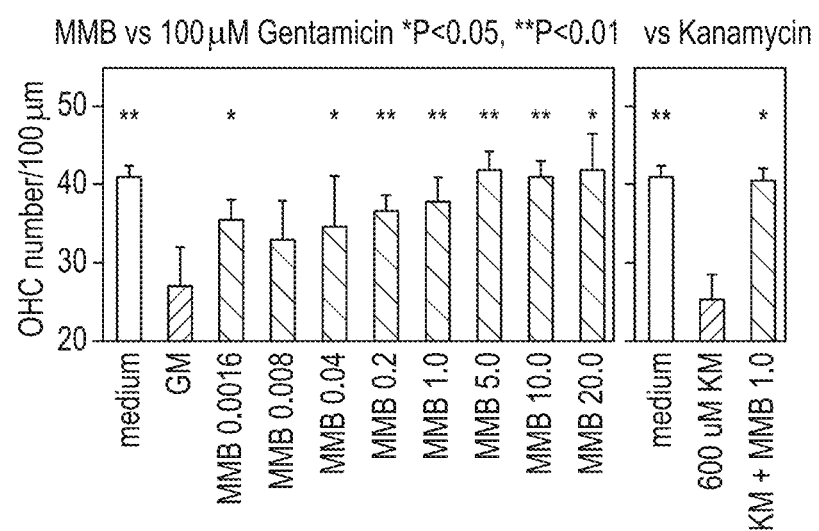

In various aspects, the compounds of this invention can be used in combination with one or more other drugs, in the form of a kit, to prevention, control, amelioration, or reduction of risk of hearing impairments, when the other drugs can have been known to impair hearing such as an antibiotic. Certain antibiotics, especially aminoglycosides (such as gentamicin, streptomycin, and neomycin). Hearing-related side effects from these antibiotics are most common in people who have kidney disease or who already have ear or hearing problems Now referring to FIG. 2A-B, Momelotinib protects from aminoglycoside toxicity in cochlear explants of P3 FVB mice. FVB mice were bred in the Creighton University animal facility. Procedures were approved by the IACUC committee of the Creighton University. 2A) Inner ears were collected from the post-natal day 3 (P3) FVB mice and transferred onto a filter (Millicell, PICM03050; Millipore) soaked in culturing medium. The filter was placed in 6-well culture plates with 1.2 mL medium outside the filter. The culturing medium is DMEM (10565-018; gibco) with 1% FBS (16000-044; gibco), 500 μL ampicillin (A5354; Sigma), 100 μL N-2 supplement (17502-048, gibco) and 100 μL B-27 supplement (17504-044, gibco). After culturing for 24 h at 37° C. in 5% CO2, 1 mL culturing medium with MMB at 0.2 μM, 200 μM MMB alone or without MMB and added both inside and outside the filter to preincubate for another 1 h before adding gentamicin solution. A 50 μg/mL gentamicin (G1397, Sigma) was chosen to induce around 35% hair cell death after incubation for 24 h at 37° C. For compound CYT-387 or MMB (A10263, AdooQ). The procedures were performed under sterile condition in the culture hood. Cochleae were then fixed with 4% PFA for 30 min and stained with Alexa Fluor 555 phalloidin in to determine the survival rate of the hair cells. All the cochleae images were taken with Zeiss 700 confocal microscopy. Immunofluorescent images of cochlea stained with phalloidin (red) at the middle turn region shows minimal levels of hair cell loss when cotreated with MMB and GM. The survival OHCs were then normalized to 100 μm length to further compare between different experimental conditions. 2B) OHC survival (OHC number per 100 μm length of cochlear middle turn) after treatment with Momelotinib at 0.0016, 0.008, 0.04, 0.2, 1.0, 5.0, 10.0 and 20.0 μM for 1 hour and co-incubated with 100 μM GM for 1 hour, or co-incubated with 600 μM kanamycin (K0254, Sigma) for 1 hour. (Mann-Whitney U Test, *13<0.05, **P<0.01). Quantification of outer hair cells from immunofluorescent images shows that cotreatment with Momelotinib grants full protection against aminoglycoside-induced hair cell loss (n=5 per group, student's t-test). * P<0.05, data shown as mean±standard error in all panels.

Figure 3A:
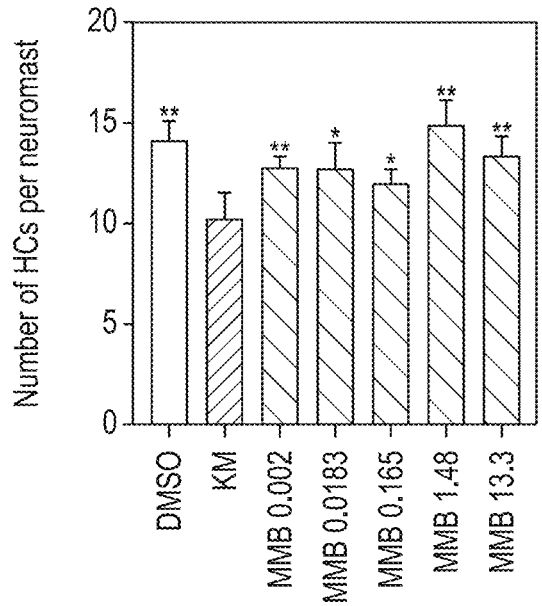
FIG. 3A-C show Momelotinib (MMB) protected zebrafish mechanosensory hair cells against gentamicin (GM) and kanamycin (KM) in vivo. 5dpf Tg(Brn3c:mGFP) larvae were used for the experiments. 3A and 3B were treated with KM (200 uM for 1 hour and 150 uM for 6 hours, respectively) and 3C was treated with GM (100 uM for 1 hour). Each treatment was pretreated with MMB at the prescribed doses prior to co-treatment with the aminoglycoside. Control animal were treated with DMSO (−) or KM or GM alone (+) Animals were then fixed and immunostained for GFP and otoferlin. Quantification was done by assessing three neuromasts in the same anatomic location of each animal (n=5). The data is plotted as mean+SD. Statistical testing was done with One-way ANOVA and Dunnett post-hoc test (*P<0.05, P<0.01,*P<0.001).
Figure 3C:
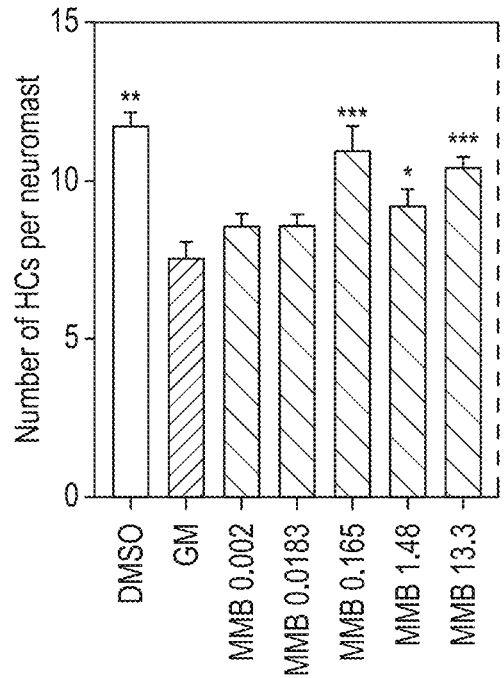
Figure 3B:
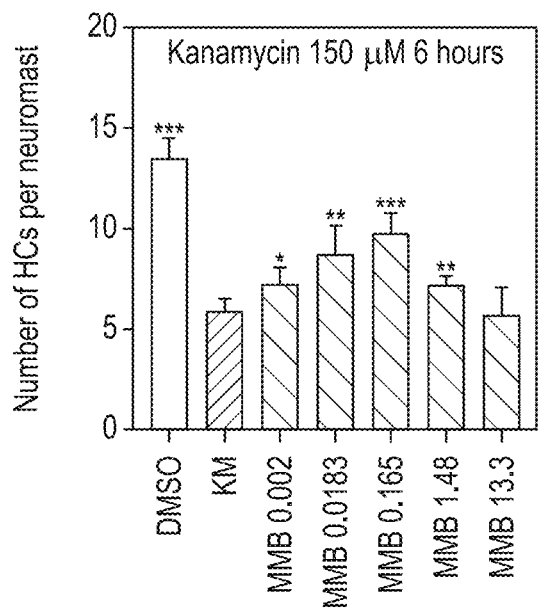

Now referring to FIG. 3A-C, Momelotinib protects from aminoglycoside induced hair cell loss in zebrafish lateral line neuromasts in vivo. Zebrafish lateral line neuromast HC counts are commonly used in vivo models for screening otoprotectants. *Danio rerio* experimental larvae were obtained by pair mating of adult fish maintained at Creighton University by standard methods approved by the Institutional Animal Care and Use Committee. We used Tg(pou4f3:mGFP) expressing a membrane bound GFP in HCs. Experimental fish were maintained at 28.5° C. in E3 media (5 mM NaCl, 0.17 mM KCl, 0.33 mM CaCl2) and 0.33 nM MgSO4, pH 7.2). Animals were cryoanaesthetized after drug treatment and prior to fixation. The neuromasts inspected, SO3 and O1-2, were part of the cranial system and included the otic, middle, and opercular neuromasts. The lateral-line neuromasts of zebrafish are a valuable system for testing protectivity of compounds against aminoglycoside toxicity in vivo, as their HCs are considered homologous to those in the mammalian inner ear and are readily accessible to drugs. For the screenings, 5-day post-fertilization (dpf) Tg(brn3c:GFP) larvae were pre-incubated with Momelotinib at 0.002, 0.018, 0.165, 1.48, and 13.3 μM for 1 hour followed by co-incubation with either 200 μM KM for 1 hour, 150 μM KM for 6 hours, or 100 μM GM for 1 hour. DMSO at μM was used as a control.

Subsequently, animals were transferred to E3 water for 5 hours and fixed in 4% paraformaldehyde (PFA) overnight (26). Neuromast HCs were immunolabeled with anti-otoferlin (HCS-1, DSHB) and anti-GFP (NB100-1614, Novus Biologicals).

These two markers were used to detect and count neuromast HCs to reduce the chances of missing some of the HCs after the treatment since we previously noticed that incubation with the compounds can affect GFP expression more difficult to detect under a fluorescence microscope (26). Otic, middle, and opercular neuromasts were identified, and HCs at SO3 (supraorbital line neuromast) and O1-2 (Otic line neuromasts) were manually counted using a Zeiss AxioSkop 2 fluorescence microscope with a 40x oil objective. Compounds were then evaluated on efficiency and potency, with the top-rated compounds showing high protection at lower concentrations.

Figure 4A:
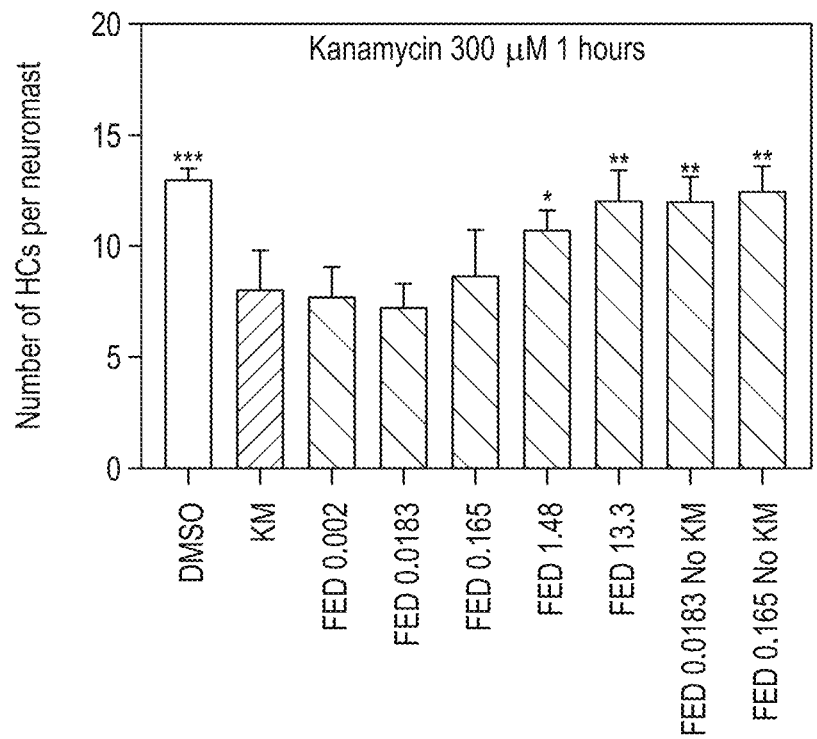
FIG. 4A-B show Fedratinib (FED) protected zebrafish mechanosensory hair cells against kanamycin (KM) in vivo. 5dpf Tg(Brn3c:mGFP) larvae were used for the experiments. Each treatment was pretreated FED at the prescribed doses prior to co-treatment with the aminoglycoside. 3A shows co-treatment with KM at 300 uM for 1 hour. 3B shows co-treatment with KM at 150 uM for 6 hours. Control animal were treated with DMSO (−) or KM alone (+) Animals were then fixed and immunostained for GFP and otoferlin. Quantification was done by assessing three neuromasts in the same anatomic location of each animal (n=5). The data is plotted as mean+SD. Statistical testing was done with One-way ANOVA and Dunnett post-hoc test (*P<0.05, P<0.01,*P<0.001).
Figure 4B:
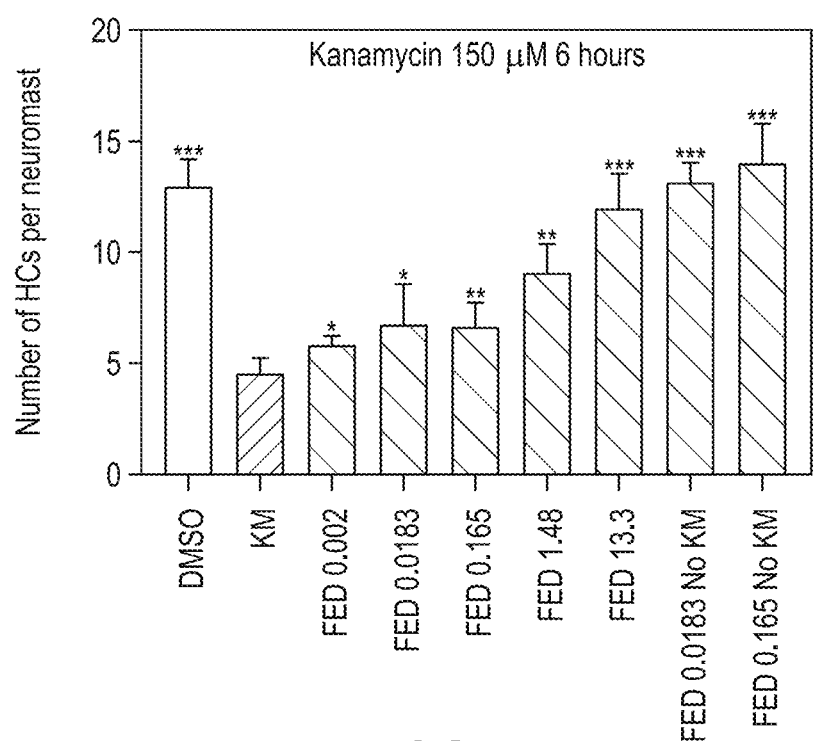

Now referring to FIG. 4A-B, Fedratinib (FED) protects from aminoglycoside induced hair cell loss in zebrafish lateral line neuromasts in vivo. For the screenings, 5-day post-fertilization (dpf) Tg(brn3c:GFP) larvae were pre-incubated with Fedratinib at 0.002, 0.018, 0.165, 1.48, and 13.3 μM for 1 hour followed by co-incubation with either 300 μM KM for 1 hour or 150 μM KM for 6 hours. DMSO at μM was used as a control. Additionally, 5-day post-fertilization (dpf) Tg(brn3c:GFP) larvae were pre-incubated with Fedratinib at, 0.018, 0.165 μM for 1 hour without being followed by co-incubation with KM.

Figure 5:
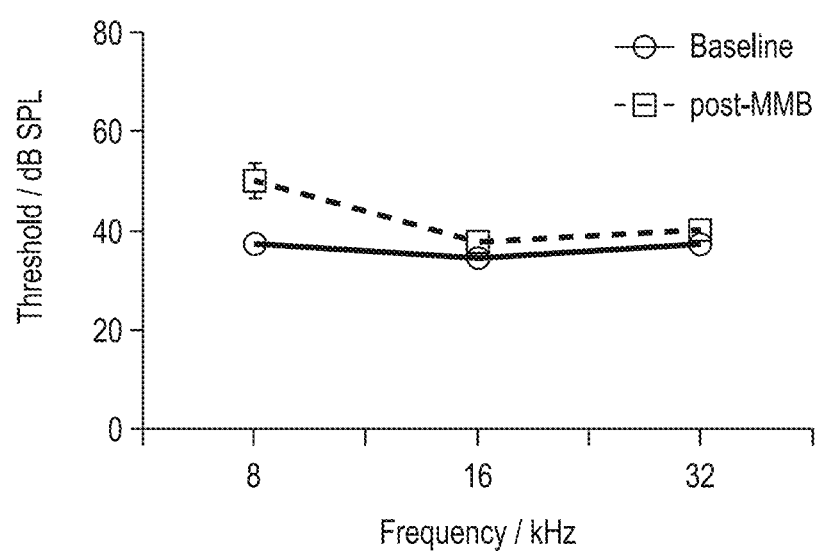
FIG. 5 shows Momelotinib is not toxic in C57BL/6 mice (4-week-old) in vivo up to a dose of 100 mg/kg/day over a 14-day treatment regimen. Oral administration of Momelotinib did not result in any general or inner ear toxicity, measured as and hearing function in 28-day old C57BL/6 mice. Auditory brainstem response (ABR) thresholds were recorded for 3 frequencies (8 kHz, 16 kHz, and 32 kHz) before and after a 14-day MMB treatment protocol. No differences were observed across all frequencies tested. Statistical analysis was done with repeated measures ANOVA between groups.

Now referring to FIG. 5, Momelotinib showed no inner ear toxicity in C57BL/6 mice. 4-week-old C57BL/6 mice obtained from The Jackson Laboratory were used, with a mix of males and females across experiments. Mice were administered a 14-day Momelotinib treatment protocol. Auditory Brainstem Response thresholds were recorded at 8 kHz, 16 kHz, and 32 kHz for a baseline sample of mice and the mice administered Momelotinib. No differences were observed across all frequencies tested.

All publications, patents and patent applications mentioned in this specification are herein incorporated by reference to the same extent as if each individual publication, patent, or patent application was specifically and individually indicated to be incorporated by reference.

Teitz T, Fang J, Goktug A N, Bonga J D, Diao S, Hazlitt R A, Iconaru L, Morfouace M, Currier D, Zhou Y, Umans R A, Taylor M R, Cheng C, Min J, Freeman B, Peng J, Roussel M F, Kriwacki R, Guy R K, Chen T, Zuo J. CDK2 Inhibitors as Candidate Therapeutics for Cisplatin- and Noise-Induced Hearing Impairment. J Exp Med. 2018 Apr. 2; 215(4):1187-1203.

While the invention has been described with reference to details of the illustrated embodiments, these details are not intended to limit the scope of the invention as defined in the appended claims. The embodiment of the invention in which exclusive property or privilege is claimed is defined as follows:

The invention claimed is:

1. A method to prevent or treat hearing loss comprising: administering to a mammal-in need thereof an effective amount of a pharmaceutical composition containing a therapeutically active agent, wherein the therapeutically active agent is momelotinib.

2. The method of claim 1, comprising protecting the inner ear cells from death caused by an antibiotic.

3. The method of claim 2, wherein the antibiotic is an aminoglycoside.

4. The method of claim 1, comprising protecting the inner ear cells from death caused by noise.

5. The method of claim 1, comprising protecting the inner ear cells from death caused by cisplatin treatment.

6. A kit comprising: an active agent, wherein the active agent is momelotinib or a pharmaceutically acceptable salt thereof; and one or more of:
(A) at least one antibiotic;
and (B) at least one cancer drug.

7. The kit of claim 6, wherein the at least one antibiotic is an aminoglycoside.

8. The kit of claim 6, wherein the at least one cancer drug is cisplatin.

* * * * *

UNITED STATES PATENT AND TRADEMARK OFFICE
CERTIFICATE OF CORRECTION

PATENT NO. : 11,766,440 B1
APPLICATION NO. : 18/117852
DATED : September 26, 2023
INVENTOR(S) : Jian Zuo and Zhuo Li Page 1 of 1

It is certified that error appears in the above-identified patent and that said Letters Patent is hereby corrected as shown below:

In the Claims

In Claim 1 the word momelotinib is incorrectly spelled as mornelotinib.

Signed and Sealed this
Seventeenth Day of December, 2024

Derrick Brent
*Acting Director of the United States Patent and Trademark Office*